United States Patent [19]

Nelson

[11] Patent Number: 5,707,679
[45] Date of Patent: Jan. 13, 1998

[54] METAL PROPIONATES FOR USE AS ANIMAL FEED SUPPLEMENTS

[75] Inventor: Christopher E. Nelson, Des Moines, Iowa

[73] Assignee: Kemin Industries, Inc., Des Moines, Iowa

[21] Appl. No.: 524,350

[22] Filed: Sep. 6, 1995

Related U.S. Application Data

[63] Continuation-in-part of Ser. No. 315,557, Sep. 30, 1994, abandoned.

[51] Int. Cl.$^6$ .......................... A23K 1/16; A61K 31/555
[52] U.S. Cl. .......................... 426/635; 426/648; 426/806; 426/807; 424/245; 424/263; 424/266
[58] Field of Search .................... 426/635, 648, 426/806, 807; 424/245, 263, 266

[56] References Cited

U.S. PATENT DOCUMENTS

| | | | |
|---|---|---|---|
| 4,315,927 | 2/1982 | Evans | 424/245 |
| 4,700,000 | 10/1987 | Merkel et al. | 562/606 |
| 4,851,153 | 7/1989 | Kono et al. | 252/518 |
| 5,006,558 | 4/1991 | Poralla et al. | 514/557 |
| 5,453,277 | 9/1995 | McCoy | 424/408 |

OTHER PUBLICATIONS

Gibson, et al., *British Poultry Science*, 27:391–402 (1986).
Shippee, et al., *Poultry Science*, 58:949,954 (1979).
Flagstad, *J. Nutrition*, 111(11):1996–1999 (1981).
21 C.F.R. Section 582.80.
*Merck Index*, 9th Ed., Merck & Co., Inc. (Rahway, N.J.: 1976), pp. 242–243, 1600.
*Quantitative Analytical Chemistry*, 5th Ed., J.S. Fritz & G.H. Schenk, eds., Allyn and Bacon, Inc. (Boston: 1987), pp. 190–193.
Basolo, F. and Pearson, R.G., *Mechanisms of Inorganic Reactions*, New York, John Wiley & Sons, Inc. pp. 1, 2, and 30 (1963).
*McGraw–Hill Encyclopedia of Science and Technology*, 6th ed. vol. 16, McGraw–Hill Book Co., New York, pp. 19–20 (1987).
Evans, *Nutrition Reviews*, 38(4):137–141 (1980).
Evans, et al., *Fed. Proc.*, vol. 38, p. 703, Abst. No. 2501, Mar. 1979.
Holwerda et al., *Feedstuffs*, pp. 12–13, 23 (Jun. 19, 1995).

*Primary Examiner*—Donald E. Czaja
*Assistant Examiner*—Choon P. Koh
*Attorney, Agent, or Firm*—Welsh & Katz, Ltd.

[57] ABSTRACT

A supplemented animal feed composition comprising (a) an animal feed that is deficient in a trace metal admixed with (b) a diet-supplementing effective amount of a polyvalent metal cation propionate having the formula $M(CH_3CH_2COO^-)_x$, wherein M is a polyvalent metal cation form of said deficient metal that is selected from the group consisting of $Zn^{+2}$, $Cu^{+2}$, $Fe^{+3}$, $Fe^{+2}$, $Mn^{+2}$, $Co^{+2}$ and $Cr^{+3}$, and x is an integer equal to the cationic charge of M. The metal propionates are used as biologically available and economical sources of trace metal for supplementation in animal diets.

6 Claims, No Drawings

METAL PROPIONATES FOR USE AS ANIMAL FEED SUPPLEMENTS

CROSS-REFERENCE OF RELATED APPLICATION

This is a continuation-in-part of application Ser. No. 08/315,557, filed Sep. 30, 1994, now abandoned, whose disclosures are incorporated by reference.

DESCRIPTION

1. Technical Field

The present invention relates to the use of a polyvalent metal propionate salt for trace metal supplementation of animal feed.

2. Background of the Invention

Trace elements are essential for the nutrition of animals, playing important roles in many biochemical and physiological processes. These elements include metals that form polyvalent cations such as zinc, iron, copper, manganese, cobalt, chromium, and molybdenum. All but molybdenum have been shown to be deficient in some natural feed ingredients, necessitating the use of supplements to make the diet nutritionally complete.

The National Research Council (NRC) has established recommended levels of these trace metals in the diets of agricultural animals (livestock) such as poultry, swine, horses, dairy and beef cattle, goats, and sheep. Studies have shown that supplementing animal diets to provide NRC recommended level of a particular metal as the polyvalent cation prevents deficiency symptoms as well as benefits animal productivity.

Trace metals in the diet present as polyvalent cations are absorbed principally throughout the small intestine of most animals. Their absorption is influenced by the chemical form of the trace metal used in the diet as well as by many dietary components. The mechanism by which a metal is absorbed and transported from the intestinal lumen into plasma is complex. There is evidence to indicate that the uptake of metals at the brush border surface of the small intestine may be via an unidentified "receptor" which may require binding of free ions or prior binding to one or more absorbable ligands.

Several chemical forms of trace metals are available for supplementation of animal diets including the inorganic salts of the trace metal, metal-amino acid complexes, metal-amino acid chelate complexes, metal-proteinate complexes, and metal-polysaccharide complexes (Official Publication of American Feed Control Officials, 1995). The most commonly used trace metal forms are the inorganic salts of the polyvalent metal cations such as ferrous sulfate, zinc oxide, copper sulfate, manganese oxide, and cobalt sulfate.

The bioavailability of trace metals from polyvalent inorganic salts is variable because of poor absorption in the gastrointestinal tract. It has been reported that trace polyvalent metal ions from metal-amino acid complexes such as zinc-lysine (U.S. Pat. No. 5,061,815) and zinc-methionine (U.S. Pat. No. 3,941,818 and No. 4,021,569) and zinc- or manganese-amino acid complexes (U.S. Pat. No. 4,764,633) are more biologically available to the animal than are the same ions provided from inorganic salts because the complexes are more readily absorbed (Wedekind et al., *J. Anim. Sci.* 1992, 70:178–187).

Metal-carboxylate complexes have been reported to influence the absorption of metal cations in the gastrointestinal tract. However, these complexes such as zinc citrate and zinc picolinate have had variable results, enhancing absorption in one study and having no effect in others (Cousins, *Physiological Rev.* (1985) 65(2):238–309, 247). Zinc picolinate has been reported to enhance the absorption of zinc in humans and rats (U.S. Pat. No. 4,315,927) but not in cattle (Flagstad, *J. Nutr.* (1981) 111:1996–1999).

Metal-carboxylate complexes are to be distinguished from the metal-carboxylate salts or metal salts of carboxylic acids. Metal-carboxylate complexes or chelates are coordination compounds that include at least one coordinate bonding, whereas metal-carboxylate salts have ionic bonding and are organic salts similar to inorganic salts.

Metal carboxylate salts have been used as animal feed supplements. Zinc acetate, cobalt acetate, and manganese acetate are approved by the Food and Drug Administration as sources of the trace metal, zinc, cobalt, and manganese, respectively, and are generally recognized as safe when added at levels consistent with good feeding practice (21 CFR section 582.80). However, zinc acetate is reported to be toxic to chickens (Gibson et al., *British Poultry Sci.* (1986) 27:391–402) and may not be palatable to ruminants.

Although several chemical complexes of trace polyvalent metal cations are commercially available and provide polyvalent metal cations that are more biologically available than are those cations provided from inorganic salts, the complexes are also more expensive. There is therefore a need for a polyvalent metal cation-containing feed supplement material that is palatable to animals, biologically available and nontoxic as well as economical to use as a source of trace polyvalent metal ions in the diet of animals.

BRIEF SUMMARY OF THE INVENTION

The present invention relates to a supplemented animal feed composition of a polyvalent metal salt of propionic acid; i.e., a polyvalent metal propionate. The composition comprises an animal feed deficient in a trace metal that is admixed with a diet-supplementing effective amount of a polyvalent metal cation propionate having the formula, $M(CH_3CH_2COO^-)_x$, wherein M is a polyvalent metal cation selected from the group consisting of zinc ($Zn^{+2}$), copper(II) ($Cu^{+2}$), iron ($Fe^{+2}$, $Fe^{+3}$) manganese ($Mn^{+2}$), cobalt ($Co^{+2}$), and chromium ($Cr^{+3}$), and x is an integer equal to the cationic charge of M.

A process for the nutritional supplementation of animals is also contemplated. That process comprises feeding animals (livestock) whose feed is deficient in a trace metal selected from the group consisting of iron, copper, zinc, manganese, cobalt and chromium using that deficient feed admixed with an amount of a propionate of the deficient polyvalent trace metal cation sufficient to overcome the trace metal deficiency of that feed; i.e., a diet-supplementing effective amount. Usually, the amount of polyvalent trace metal propionate added is sufficient to provide a total trace metal cation amount that is at least equal to the NRC recommended level.

An advantage of this invention is that it provides polyvalent metal propionate compounds as a source of polyvalent trace metals to supplement animal feed in a form that is palatable to the animal, nontoxic and can be readily absorbed by the animal. Another advantage of this invention is that it provides a supplement that is readily utilizable in animal diets. A benefit of this invention is that it provides a supplement that is economical to use. Still further advantages and benefits of the invention will be apparent to a worker of ordinary skill from the description that follows.

DETAILED DESCRIPTION OF THE INVENTION

The present invention relates to the use of a polyvalent trace metal propionate alone or in combination with any other trace metal propionate as a dietary supplement for trace metal-deficient feeds for livestock (animals) such as cattle, swine, sheep, goats, horses and poultry.

A supplemented animal feed composition is contemplated. That feed is comprised of (a) an animal feed that is deficient in a before-discussed trace metal that is admixed with (b) a polyvalent metal cation propionate of the formula $M(CH_3CH_2COO^-)_x$, wherein M is a polyvalent metal cation selected from the group consisting of zinc ($Zn^{+2}$), copper(II) ($Cu^{+2}$), iron ($Fe^{+2}$, $Fe^{+3}$) manganese ($Mn^{+2}$), cobalt ($Co^{+2}$), and chromium ($Cr^{+3}$), and x is an integer equal to the cationic charge of M. A polyvalent metal cation propionate is present in an amount sufficient to provide an amount of polyvalent metal cation to the blood stream that is at least the recommended level of the trace metal; i.e., a diet-supplementing effective amount. An amount sufficient to provide twice the recommended amount is also sometimes used, particularly with swine and sheep, in times of stress upon those animals or when used in starter rations.

It is also to be understood that the supplemented animal feed can contain one or more, up to all of the before-defined trace metal propionates. Inasmuch as the trace elements are normally not present in equal amounts in a given feed and are not equally deficient, differing amounts of supplemental trace metal propionate are present in the same supplemental feed. In addition, differing feeds contain differing amounts of a supplemental trace metal propionate are contemplated.

The amount of trace polyvalent metal propionate that is added can be determined from the molecular weight of the particular propionate and knowledge concerning the trace metal amount or deficiency of the feed to be used. The amount of trace metal present in a given feed can be obtained by analysis or resort to average values for the feed type used as are published in the literature.

A contemplated polyvalent trace metal propionate is relatively non-toxic, with the major toxicity coming from the polyvalent metal ion. Toxicity values of various metals for domestic animals are also available in the literature and are available from the National Academy of Sciences/National Research Council in Washington, D.C.

A process for the nutritional enhancement of animals (livestock as discussed before) is also contemplated. Here, an animal whose feed is deficient in a before-described trace metal is fed with a composition of that deficient feed supplemented with a before-discussed polyvalent trace metal cation propionate of the formula $(CH_3CH_2CO_2^-)_xM$. That polyvalent trace metal cation propionate is used in at least a diet-supplementing effective amount.

As discussed before for the supplemented animal feed, one or more than one polyvalent trace metal cation propionate can be used in this process. Where more than one polyvalent trace metal cation propionate is used, it is preferred, but not required that each added propionate provide a recommended level for its trace metal. A supplemented animal feed described before therefore need have only one trace metal supplemented to at least a diet-supplementing effective amount, with other supplemented trace metals being present at less than that amount.

A contemplated polyvalent metal cation propionate can be prepared in a number of ways. Such compounds are typically prepared by reaction of a basic compound of the polyvalent metal cation such as an oxide, hydroxide or carbonate in an aqueous solution with a required amount of propionic acid. After the neutralization is completed, the water is then removed and the propionate is recovered by a conventional technique such as spray or freeze drying or a crystallization procedure. An ion exchange reaction in which an aqueous solution of a water-soluble form of the polyvalent metal cation is contacted with an anion exchange resin in propionate form can be used to effect the anion exchange. The propionate salt is then recovered as discussed before.

A contemplated diet-supplementing amount of a polyvalent metal cation propionate can be admixed with the animal feed by any convenient means. Exemplary procedures include dry mixing of the propionate supplement with the dry feed and spraying an aqueous solution of the propionate supplement on the animal feed that is typically being agitated during the addition.

The following examples illustrate but do not limit a product and process of the invention.

EXAMPLE 1

Comparative Zinc Bioavailability

A study was conducted to compare the relative biological availability of zinc propionate, zinc methionine and zinc sulfate. The zinc preparations were added to the basal feed of day-old broilers at the levels indicated in Table 1. Each zinc treatment was replicated eight times and each pen contained ten male birds.

TABLE 1

Design of Zinc Bioavailability Trial

| Treatment ID | Source | Level mg/kg | Pen | | | | | | | |
|---|---|---|---|---|---|---|---|---|---|---|
| 1 | Zinc propionate | 10 | 13 | 8 | 21 | 22 | 35 | 30 | 49 | 68 |
| 2 | Zinc propionate | 20 | 25 | 20 | 33 | 16 | 5 | 18 | 67 | 56 |
| 3 | Zinpro ® | 10 | 1 | 14 | 3 | 34 | 29 | 12 | 79 | 86 |
| 4 | Zinpro ® | 20 | 31 | 2 | 9 | 46 | 17 | 48 | 55 | 74 |
| 5 | Zinc sulfate | 0 | 37 | 44 | 27 | 10 | 23 | 36 | 91 | 50 |
| 6 | Zinc sulfate | 10 | 19 | 38 | 15 | 28 | 47 | 42 | 73 | 92 |
| 7 | Zinc sulfate | 20 | 43 | 32 | 45 | 40 | 11 | 24 | 85 | 62 |
| 9 | Zinc sulfate | 30 | 7 | 26 | 39 | 4 | 41 | 6 | 61 | 80 |

Zinpro ® = Zinc methionine bisulfate; Zinpro Corporation, Minneapolis, MN.

Basal feeds and zinc compound were mixed in a horizontal feed mixer providing the desired ingredient composition as shown in Table 2. The broilers were fed the rations for 21 days. Feed weights were taken during the trial. Body weights were measured at the beginning and at the end of the trial. On day 21, zinc levels in the blood and tibia ash were determined. The assay procedures for total tibia zinc content or concentration to assess zinc utilization are similar to those used by Wedekind et al., *J. Anim. Sci.*, 70:178–187 (1992). The data were analyzed according to the SAS statistical package.

TABLE 2

| Formulation and Approximate Analysis of Basal Feed | |
|---|---|
| Ingredient | Percent |
| Corn yellow | 57.060 |
| Soybean meal - 48% | 34.621 |
| Fat | 3.096 |
| DL methionine[1] | 2.339 |
| Salt | 0.289 |
| Limestone | 0.621 |
| Defluorinated phosphate | 1.724 |

TABLE 2-continued

Formulation and Approximate
Analysis of Basal Feed

| Ingredient | Percent |
|---|---|
| Vitamin premix | 0.050 |
| Trace min. premix[2] | 0.050 |
| Biocox[3] | 0.100 |
| Bacitracin MD-50[4] | 0.050 |

[1]DL methionine is used to equalize methionine in all ratios.
[2]Trace mineral premix does not contain zinc.
[3]Available from Hoffmann-LaRoche, Inc., Nutley, NJ.
[4]Available from A.L. Laboratories, Ft. Lee, NJ.

Chick growth parameters and zinc levels in the blood and tibia ash were used as criteria to determine the biological availability of zinc. The broilers fed with zinc propionate had the same ending body weight as the broilers fed with zinc methionine at both the 10 mg/kg and 20 mg/kg levels. Both organic sources provided statistically significant higher ending body weights than did zinc sulfate at both the 10 mg/kg and mg/kg levels. A similar set of results was seen for weight gain over the 21 day trial. Additionally, broilers fed with zinc propionate and zinc methionine showed comparable levels of zinc in the blood and tibia ash on day 21. With these data, a relative biological availability for zinc propionate and zinc methionine can be calculated. The summary of this calculation is shown in Table 3 below. The biological availability of zinc sulfate was arbitrarily set at 100%. For all parameters, there was no statistically significant difference between zinc propionate and zinc methionine with the exception of feed conversion. There was a slight advantage in the broilers treated with zinc propionate compared to zinc methionine. It can thus be concluded that zinc propionate showed equal biological availability and equal performance enhancement as zinc methionine.

TABLE 3

Relative Biological Availability (%)*

| Criterion | Sulfate | Propionate | Zinpro ® |
|---|---|---|---|
| Ending body weight (lbs) 21 days | 100.00[b] | 128.21[a] | 132.46[a] |
| Body weight gain (lbs) 21 days | 100.00[b] | 128.24[a] | 131.52[a] |
| Feed conversion (corr.) 3–21 days | 100.00[a] | 100.30[a] | 90.38[b] |
| Bone ash (%) 21 days | 100.00[b] | 113.18[a] | 113.95[a] |
| Tibia ash zinc (µg/g) | 100.00[b] | 125.67[a] | 123.99[a] |
| Plasma Zinc (µg/ml) | 100.00[b] | 113.33[a] | 124.00[a] |

*Means within a row grouping without a common superscript are significantly different (P < 0.05) as determined by Least Significant Difference.

EXAMPLE 2

Influence of Zinc Propionate on Performance of Growing and Finishing Cattle

The present studies were conducted to compare zinc propionate to zinc methionine and inorganic zinc sulfate as sources of zinc for growing and finishing cattle.

Study 1: Finishing Cattle

Fifty-six Angus crossbred steers were used in this study. Steers were purchased from either a feeder calf sale only a preconditioned sale. Steers were blocked by sale type and weight, and then randomly assigned to a feed regimen. Those regimens were: 1) inorganic zinc sulfate (control), 2) zinc propionate and 3) zinc methionine as supplements to a basal feed. All regimens provided 25 ppm of supplemental zinc. Steers were housed in pens containing seven steers each. The control regimen had two replicate pens of cattle head), whereas the two organic zinc regimens had three replicate pens of steers (21 head each).

Steers were fed ad libitum the high concentrate basal finishing diet shown in Table 4. Supplemental protein was supplied from a combination of soybean meal and urea. Steer weights were obtained on two consecutive days at the beginning and the end of the 140-day study. Interim weights were taken at 28-day intervals. Feed intake was measured daily. Blood and rumen fluid samples were obtained from 10 steers per treatment approximately two hours post feeding on day 42 of the study. Samples were analyzed for plasma and rumen fluid soluble zinc concentrations. Data were analyzed statistically by least square analysis of variance.

TABLE 4

Composition of Basal Diet

| Ingredient | Percent |
|---|---|
| Corn, ground | 86.61 |
| Hay, ground | 8.00 |
| Soybean meal | 3.00 |
| Urea | 0.75 |
| Calcium carbonate | 1.10 |
| Potassium chloride | 0.30 |
| Salt | 0.20 |
| Vitamins A, D & E | 0.04 |
| Trace minerals[a] | ++ |
| Monensin[b] | ++ |

[a]Supplied 18.9 mg of Mn, 15.0 mg of Cu, 0.1 mg of Se, 0.17 mg of Co and 0.55 mg of I per kg of diet.
[b]Added to supply 20 g monensin/ton of diet.

Performance results from cattle in the finishing study are shown in Table 5. Average daily gain, feed intake and gain/feed are shown by 28-day period and for the entire 140-day study.

TABLE 5

Effect of Zinc Source on Performance of Finishing Steers

| | Zinc Source | | | |
|---|---|---|---|---|
| Item | Sulfate | Propionate | Methionine | SE |
| Initial weight, kg | 303.0 | 302.9 | 304.7 | 0.9 |
| Final weight, kg | 489.6 | 487.5 | 487.6 | 9.6 |
| Average daily gain | | | | |
| 0 to 28 days | 1.26 | 1.38 | 1.32 | 0.04 |
| 29 to 56 days | 1.46 | 1.57 | 1.45 | 0.14 |
| 57 to 84 days | 1.52 | 1.40 | 1.57 | 0.07 |
| 85 to 112 days | 1.19 | 1.08 | 0.97 | 0.10 |
| 113 to 140 days | 1.24 | 1.17 | 1.22 | 0.14 |
| Total (0 to 140 days) | 1.33 | 1.32 | 1.31 | 0.07 |
| Feed intake, kg/d | | | | |
| 0 to 28 days | 6.28 | 6.30 | 6.35 | 0.10 |
| 29 to 56 days | 7.51 | 8.09 | 7.76 | 0.35 |
| 57 to 84 days | 6.21 | 6.35 | 6.43 | 0.07 |
| 85 to 112 days | 8.33 | 8.69 | 8.51 | 0.18 |
| 113 to 140 days | 6.60 | 6.63 | 6.59 | 0.28 |
| Total (0 to 140 days) | 6.99 | 7.21 | 7.13 | 0.18 |
| Gain/feed | | | | |
| 0 to 28 days[a,b] | 0.201 | 0.219 | 0.208 | 0.004 |
| 29 to 56 days | 0.195 | 0.194 | 0.186 | 0.012 |
| 57 to 84 days | 0.244 | 0.222 | 0.244 | 0.013 |

TABLE 5-continued

Effect of Zinc Source on Performance of Finishing Steers

| | Zinc Source | | | |
|---|---|---|---|---|
| Item | Sulfate | Propionate | Methionine | SE |
| 55 to 112 days | 0.142 | 0.124 | 0.115 | 0.009 |
| 113 to 140 days | 0.189 | 0.176 | 0.184 | 0.017 |
| Total (0 to 140 days) | 0.191 | 0.183 | 0.183 | 0.006 |

[a]Zinc propionate vs. zinc sulfate (P < 0.05).
[b]Zinc propionate vs. zinc methionine (P < 0.10).

As is seen, feed intake and daily gain were similar across the feed regimens. Steers fed zinc propionate had a greater gain/feed ratio during the first 28 days than cattle fed zinc sulfate (P<0.05) or zinc methionine (P<0.10). However, over the entire 140-day period, feed efficiency was not affected by treatment.

Zinc concentrations in plasma were not affected by feed regimen and were in the normal range. Rumen fluid soluble zinc concentrations were higher than anticipated based on previous studies. However, no significant differences were observed between feed regimens in ruminal soluble zinc concentrations.

Study 2: Growing Cattle

Thirty-six Angus steers with an average body weight of 268 kg were stratified by weight and randomly assigned to feed regimens. Those regimens were: 1) zinc sulfate (control), 2) zinc propionate and 3) zinc methionine as supplements to a basal feed. Zinc was supplemented in all treatments to provide 25 ppm of supplemental zinc.

Steers were housed in pens of 12 steers and individually fed using electronic gates. Each pen contained an equal number of steers from each dietary regimen. Steers were fed a basal corn silage-based growing diet supplemented with protein, minerals and vitamins. Composition of the basal diet is shown in Table 6. Diets were offered ad libitum.

TABLE 6

Composition of Basal Diet

| Ingredient | Percent[a] |
|---|---|
| Corn, silage | 90.00 |
| Corn | 3.98 |
| Soybean meal | 4.60 |
| Urea | 0.75 |
| Calcium carbonate | 0.43 |
| Salt | 0.20 |
| Vitamins A, D & E | 0.04 |
| Trace minerals | ++[b] |

[a]Dry matter basis.
[b]Supplied 18.9 mg of Mn, 15.0 mg of Cu, 0.1 mg of Se, 0.17 mg of Co and 0.55 mg of I per kg of diet.

Body weights were obtained on two consecutive days at the initiation and termination of the 112-day study. Interim weights were taken at 28-day intervals. Blood and rumen fluid samples were obtained on day 42 of the study for determination of plasma and rumen fluid soluble zinc concentrations. Data were statistically analyzed by least square analysis of variance.

Table 7 shows performance results from the growing study. During the second 28-day period (29 to 56 days), gains were greater (P<0.05) in steers fed zinc methionine compared with those fed zinc propionate. Gains for the entire study were not significantly affected by treatment but tended to be higher for steers fed zinc methionine. Steers fed either zinc propionate or zinc methionine consumed more (P<0.10) feed over the total study period than steers fed zinc sulfate. For the total 112-day study, steers fed zinc propionate had a lower gain/feed ratio than those fed zinc sulfate (P<0.05) or zinc methionine (P<0.10). It is unclear why efficiency of gain was lower in steers fed zinc propionate.

TABLE 7

Effect of Zinc Source on Performance of Growing Steers

| | Zinc Source | | | |
|---|---|---|---|---|
| Item | Sulfate | Propionate | Methionine | SE |
| Initial weight, kg | 265.5 | 269.5 | 267.7 | 1.9 |
| Final weight, kg | 391.8 | 393.1 | 399.6 | 4.3 |
| Average daily gain, kg | | | | |
| 0 to 28 days | 1.34 | 1.33 | 1.33 | 0.09 |
| 29 to 56 days[a] | 1.10 | 0.96 | 1.18 | 0.07 |
| 57 to 84 days | 0.72 | 0.74 | 0.87 | 0.07 |
| 85 to 112 days | 1.36 | 1.30 | 1.34 | 0.06 |
| Total (0 to 112 days) | 1.13 | 1.10 | 1.18 | 0.04 |
| Feed intake, kg/d | | | | |
| 0 to 28 days | 7.67 | 8.39 | 8.11 | 0.34 |
| 29 to 56 days | 8.13 | 8.89 | 9.03 | 0.38 |
| 57 to 84 days[b,c] | 7.62 | 8.53 | 8.62 | 0.37 |
| 85 to 112 days | 7.86 | 8.60 | 8.56 | 0.36 |
| Total (0 to 112 days) | 7.82 | 8.60 | 8.58 | 0.31 |
| Gain/feed | | | | |
| 0 to 28 days[a,b] | 0.178 | 0.159 | 0.164 | 0.011 |
| 29 to 56 days[d,e] | 0.137 | 0.106 | 0.132 | 0.009 |
| 57 to 84 days | 0.095 | 0.086 | 0.104 | 0.008 |
| 85 to 112 days | 0.174 | 0.162 | 0.158 | 0.009 |
| Total (0 to 112 days)[d,e] | 0.145 | 0.128 | 0.139 | 0.004 |

[a]Zinc propionate vs. zinc methionine (P < 0.05).
[b]Zinc propionate vs. zinc sulfate (P < 0.10).
[c]Zinc propionate vs. zinc sulfate (P < 0.10).
[d]Zinc propionate vs. zinc sulfate (P < 0.05).
[e]Zinc propionate vs. zinc methionine (P < 0.10).

Steers given zinc propionate had higher plasma zinc concentrations on day 42 than steers supplemented with zinc sulfate. Plasma zinc was similar in steers fed the two organic zinc sources. Rumen fluid soluble zinc concentrations were similar across regimens.

The foregoing description and the examples are intended as illustrative and are not to be taken as limiting. Still other variations within the spirit and scope of this invention are possible and will readily present themselves to those skilled in the art.

I claim:

1. A supplemented animal feed composition comprising (a) an animal feed that is deficient in a trace metal admixed with (b) a diet-supplementing effective amount of a polyvalent metal cation propionate having the formula $M(CH_3CH_2COO^-)_x$, wherein M is a polyvalent metal cation form of said deficient metal that is selected from the group consisting of $Zn^{+2}$, $Cu^{+2}$, $Fe^{+3}$, $Fe^{+2}$, $Mn^{+2}$, $Co^{+m}$ and $Cr^{+3}$, and x is an integer equal to the cationic charge of M.

2. The composition of claim 1 wherein the polyvalent metal cation is zinc.

3. The composition of claim 1 wherein the polyvalent metal cation is copper.

4. A process for the nutritional supplementation of animals that comprises feeding animals whose feed is deficient in a trace metal selected from the group consisting of zinc, copper, iron, manganese, cobalt and chromium using a supplemented feed comprising that deficient feed admixed with a diet-supplementing effective amount of a polyvalent metal cation propionate having the formula $M(CH_3CH_2COO^-)_x$ wherein M is a polyvalent metal cation selected from the group consisting of $Zn^{+2}$, $Cu^{+2}$, $Fe^{+3}$, $Fe^{+2}$, $Mn^{+2}$, $Co^{+2}$ and $Cr^{+3}$, and x is an integer equal to the cationic charge of M.

5. The process of claim 4 wherein the polyvalent metal cation is zinc.

6. The process of claim 4 wherein the supplemented amount of polyvalent metal cation propionate provides about twice the recommended level of said trace metal.

* * * * *